United States Patent [19]

Gibbs et al.

[11] 4,143,078

[45] Mar. 6, 1979

[54] FLUORINATION OF METHYL KETONES

[75] Inventors: Marylu B. Gibbs; Gordon Liu, both of Baton Rouge, La.

[73] Assignee: The Dow Chemical Company, Midland, Mich.

[21] Appl. No.: 908,036

[22] Filed: May 22, 1978

[51] Int. Cl.² ............................................. C07C 17/22
[52] U.S. Cl. ............................... 260/653.6; 260/653.7
[58] Field of Search ........................... 260/653.6, 653.7

[56] References Cited

U.S. PATENT DOCUMENTS

| | | | |
|---|---|---|---|
| 2,859,245 | 11/1958 | Smith | 260/544 |
| 2,972,639 | 2/1961 | Stevens | 260/653.8 |

Primary Examiner—C. Davis

[57] ABSTRACT

Methyl ketones such as acetone, methyl ethyl ketone, and methyl isobutyl ketone react with vaporized aqueous HF in the vapor phase at about 190° C.–400° C. to make the corresponding 2,2-difluoroalkanes.

4 Claims, No Drawings

FLUORINATION OF METHYL KETONES

BACKGROUND OF THE INVENTION

The present invention is a new chemical process, more particularly, a new method for making certain difluorinated compounds.

2,2-Difluoropropane and similar gem-difluoroalkanes are useful as aerosol propellants, refrigerants, blowing agents for making foamed plastics, or as chemical intermediates for making such substances. These compounds have been made in the past by reacting acetone and other methyl ketones with fluorinating agents such as $SF_4$ (U.S. Pat. No. 2,859,245), $BrF_3$ (U.S. Pat. No. 2,972,639), and combinations of $BrF_3$ with other fluorides (U.S. Pat. No. 3,068,299). It would be advantageous to be able to use a more readily available and more easily handled fluorinating reagent to produce these compounds.

SUMMARY OF THE INVENTION

It has now been found that vaporized aqueous hydrofluoric acid of about 20–75 percent concentration reacts with a methyl ketone of 3–6 carbon atoms in the vapor phase at about 190° C.–400° C. to form the corresponding 2,2-difluoroalkane. Under preferred process conditions, the yield of the difluoroalkane is essentially 100 percent.

DETAILED DESCRIPTION OF THE INVENTION

Preferably, aqueous hydrofluoric acid having an HF concentration of about 35–40 percent by weight is used in the process, i.e., a composition approximating the water-HF azeotrope. The quantity of HF relative to the methyl ketone is not critical to operability of the process, but best results are usually obtained by using at least the stoichiometric two moles of HF per mole of ketone and preferably about 2–10 moles of HF.

The process is normally carried out at or near normal atmospheric pressure although process pressures moderately above atmospheric pressure may be of some advantage in some cases, for example, pressures in the approximate range of 1–10 atmospheres.

The reaction appears to be noncatalytic and an empty reactor may be used. However, an inert granular or otherwise porous filler in the reactor may be employed to provide better heat exchange. Granules or screens of materials such as metal fluorides, copper, Monel metal, or other such material inert to the reactants under process conditions are examples.

The process can be carried out in process equipment made of metals known to be resistant to HF in the presence of water. Such metals include copper, brass, and Monel metal as well as more exotic and usually impractical metals such as silver and platinum.

EXAMPLE 1

The reactor was a 5 cm × 25 cm Monel metal tube packed with 200 cc of granular aluminum fluoride which provided a heat transfer medium for the reaction. The aluminum fluoride was prepared by passing vaporized 38 percent aqueous HF through a bed of alumina pellets at about 300° C. until essentially all of the alumina had been converted to fluoride. The reactor was horizontally disposed within a tubular electrical furnace. Aqueous HF of 38 percent concentration and acetone were mixed to make a solution containing a 3:1 molar ratio of HF to acetone and the solution was vaporized by pumping it at an average rate of about 2.4 ml/min. through a coil of copper tubing heated at 150° C. by a sand bath. The mixed vapors passed through a heated Monel metal line to the reactor. Effluent product vapors were cooled by a water-cooled condenser and scrubbed by 10 percent aqueous NaOH before being sampled for gas chromatographic analysis.

At a reactor temperature of 360° C., 7.8 percent of the acetone feed was converted, all of the converted acetone being recovered as 2,2-difluoropropane.

When other methyl ketones are substituted for acetone in the reaction described in Example 1, similar conversions of the ketone and yields of the corresponding 2,2-difluoroalkane are obtained. In this way, methyl ethyl ketone is reacted with vaporized aqueous HF to make 2,2-difluorobutane, methyl isobutyl ketone is reacted to make 2,2-difluoro-4-methylpentane, and methyl isopropyl ketone is reacted to make 2,2-difluoro-3-methylbutane.

In batch reactions of the 38 percent aqueous HF and acetone solution of Example 1 carried out in a Monel metal pressure reactor at 140° C.–190° C. and autogenous pressure up to 85 psig, low acetone conversions were obtained and the product was a mixture of 2,2-difluoropropane, isobutylene, and tert-butyl fluoride. The presence of $AlF_3$ and $CrF_3$ had no effect on these reactions. Evidently, side reactions made the liquid phase reaction impractical.

We claim:

1. A process for making a 2,2-difluoroalkane which comprises reacting by contacting a methyl ketone of 3–6 carbon atoms in the vapor phase with vaporized aqueous HF of about 20–75 percent HF concentration at a temperature of about 190° C.–400° C.

2. The process of claim 1 wherein the aqueous HF has a concentration of about 35–40 percent.

3. The process of claim 1 wherein at least about 2 moles of HF is contacted with a mole of ketone.

4. The process of claim 1 wherein the ketone is acetone.

* * * * *